US011033426B2

(12) United States Patent
Taylor et al.

(10) Patent No.: US 11,033,426 B2
(45) Date of Patent: Jun. 15, 2021

(54) THERMAL SYSTEM

(71) Applicant: Stryker Corporation, Kalamazoo, MI (US)

(72) Inventors: Gregory S. Taylor, Kalamazoo, MI (US); Christopher John Hopper, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 517 days.

(21) Appl. No.: 15/936,860

(22) Filed: Mar. 27, 2018

(65) Prior Publication Data
US 2018/0280191 A1    Oct. 4, 2018

Related U.S. Application Data
(60) Provisional application No. 62/477,596, filed on Mar. 28, 2017.

(51) Int. Cl.
*A61F 7/08*    (2006.01)
*A61F 7/00*    (2006.01)
(Continued)

(52) U.S. Cl.
CPC .............. *A61F 7/08* (2013.01); *A61F 7/0053* (2013.01); *A61F 7/0085* (2013.01); *A61F 7/02* (2013.01);
(Continued)

(58) Field of Classification Search
CPC ........ A61F 7/08; A61F 7/0053; A61F 7/0085; A61F 7/02; A61F 7/007; A61F 7/0097;
(Continued)

(56) References Cited

U.S. PATENT DOCUMENTS 4,966,145 A  *  10/1990  Kikumoto ................. A47C 7/74
                                                   165/46
5,733,320 A      3/1998  Augustine
                          (Continued)

OTHER PUBLICATIONS

Gaymar Medi-Therm III, Hyper/Hypothermia Machine Ref MTA7912 Service Manual, Nov. 2009.
(Continued)

*Primary Examiner* — Joseph A Stoklosa
*Assistant Examiner* — Adam J Avigan
(74) *Attorney, Agent, or Firm* — Warner Norcross + Judd LLP

(57) ABSTRACT

A thermal control unit for controlling a patient's temperature includes a fluid outlet for delivering temperature-controlled fluid to a patient, a pump, first and second cooling units, and a controller that selectively enables and disables at least one of the cooling units based on one more factors, such as the temperature of the fluid. Alternatively or additionally, a variable speed fan is included in one or both of the cooling units that blows air over the condenser and the controller selectively controls the fan speed based on factors such as the temperature of the circulating fluid. The thermal control unit may be modified to accept a cartridge having its own cooling unit. When so modified, the controller communicates with a controller inside of the cartridge and coordinates control of the cartridge cooling unit and the cooling unit inside the thermal control unit that is external to the cartridge.

23 Claims, 5 Drawing Sheets

(51) Int. Cl.
  *A61F 7/02* (2006.01)
  *A61B 5/01* (2006.01)
  *A61B 5/00* (2006.01)

(52) U.S. Cl.
  CPC .............. *A61B 5/01* (2013.01); *A61B 5/4836* (2013.01); *A61B 2560/0266* (2013.01); *A61F 7/007* (2013.01); *A61F 7/0097* (2013.01); *A61F 2007/0054* (2013.01); *A61F 2007/0086* (2013.01); *A61F 2007/0095* (2013.01); *A61F 2007/0096* (2013.01); *A61F 2007/0295* (2013.01); *A61M 2205/127* (2013.01)

(58) Field of Classification Search
  CPC ...... A61F 2007/0054; A61F 2007/0086; A61F 2007/0085; A61F 2007/0295; A61F 2007/0096; A61F 2007/0095; F25B 7/00; A61B 5/4836; A61B 2560/0266; A61B 5/01; A61M 2205/127
  See application file for complete search history.

(56) References Cited

U.S. PATENT DOCUMENTS

| | | | |
|---|---|---|---|
| 6,574,975 B2 * | 6/2003 | Bourne | F24F 5/0035 62/171 |
| 6,692,518 B2 * | 2/2004 | Carson | A61F 7/0085 219/428 |
| 6,830,581 B2 | 12/2004 | Magers | |
| 7,341,050 B2 | 3/2008 | Yi | |
| 8,706,207 B2 | 4/2014 | Flint | |
| 9,599,118 B2 * | 3/2017 | Zhou | F04C 28/08 |
| 9,696,070 B2 * | 7/2017 | Ohta | F25B 41/04 |
| 2002/0092318 A1 * | 7/2002 | Tipton | F25B 39/02 62/510 |
| 2003/0196445 A1 * | 10/2003 | Cho | F25B 1/08 62/197 |
| 2007/0130976 A1 * | 6/2007 | Akehurst | F25B 49/027 62/228.5 |
| 2014/0172050 A1 * | 6/2014 | Dabrowiak | A61F 7/12 607/106 |
| 2014/0277302 A1 * | 9/2014 | Weber | A61F 7/0085 607/104 |
| 2014/0343639 A1 | 11/2014 | Hopper et al. | |
| 2015/0230975 A1 * | 8/2015 | Dabrowiak | F25B 39/02 607/105 |
| 2016/0123652 A1 | 5/2016 | Hsieh et al. | |
| 2016/0354234 A1 * | 12/2016 | Dabrowiak | A61F 7/007 |
| 2017/0266036 A1 | 9/2017 | Taylor | |

OTHER PUBLICATIONS

Altrix Precision Temperature Management System Stryker Operations Manual, Dec. 2016.
Sorin Group, Heater-Cooling System 3T, Operating Instructions, 2015.

* cited by examiner

THERMAL SYSTEM

CROSS-REFERENCE TO RELATED APPLICATIONS

This application claims priority to U.S. provisional patent application Ser. No. 62/477,596 filed Mar. 28, 2017, by inventors Gregory S. Taylor and Christopher Hopper and entitled THERMAL SYSTEM, the complete disclosure of which is incorporated herein by reference.

BACKGROUND

The present disclosure relates to a thermal control system for controlling the temperature of circulating fluid that is delivered to one or more thermal pads positioned in contact with a patient.

Thermal control systems are known in the art for controlling the temperature of a patient by providing a thermal control unit that supplies temperature controlled fluid to one or more thermal pads positioned in contact with a patient. The thermal control unit includes one or more heat exchangers for controlling the temperature of the fluid and a pump that pumps the temperature controlled fluid to the pad(s). After passing through the pad(s), the fluid is returned to the thermal control unit where any necessary adjustments to the temperature of the returning fluid are made before being pumped back to the pad(s). In some instances, the temperature of the fluid is controlled to a static target temperature, while in other instances the temperature of the fluid is varied as necessary in order to automatically effectuate a target patient temperature. The thermal control unit can therefore be used to warm or cool a patient.

The pads are placed in close contact with the patient in order to facilitate heat exchange between the patient and the pad. In one common arrangement, three pads are applied to the patient: one applied around the patient's torso, one applied around the patient's right leg, and one applied around the patient's left leg.

SUMMARY

The present disclosure provides various improved aspects to a thermal control system, including the thermal control unit and the thermal pads. These improved aspects include quieter operation of the thermal control unit, increased cooling power, better efficiency, greater portability, simpler design, and easier use. Other improved aspects of the thermal control system are also disclosed herein and described in more detail below.

According to one embodiment of the present disclosure, a thermal control unit for controlling a patient's temperature is provided. The thermal control unit includes a fluid outlet adapted to fluidly couple to a fluid supply line; a fluid inlet adapted to fluidly couple to a fluid return line; a circulation channel coupled to the fluid outlet and the fluid inlet; a pump for circulating fluid through the circulation channel from the fluid inlet to the fluid outlet; a first cooling unit in thermal communication with the circulation channel; a second cooling unit in thermal communication with the circulation channel; and a controller. The controller communicates with the first and second cooling units and selectively enables and disables the first cooling unit based at least partially upon a temperature of the fluid.

According to other aspects of the present disclosure, the first cooling unit includes a first compressor and the second cooling unit includes a second compressor. One or more of the first and second compressors are fixed speed compressors.

In another aspect, the first cooling unit has a first heat transfer capacity and the second cooling unit has a second heat transfer capacity that is different from the first heat transfer capacity.

In some embodiments, the controller also selectively enables and disables the second cooling unit based at least partially upon the temperature of the fluid. In at least one such embodiment, the controller automatically enables both the first and second cooling units when the thermal control unit initially begins cooling the fluid, and thereafter automatically disables one of the first and second cooling units based at least partially upon the temperature of the fluid.

According to another aspect, the thermal control unit further includes a patient temperature port adapted to receive a patient temperature probe that detects the patient's temperature. The patient temperature port communicates the patient's temperature to the controller, and the controller selectively enables and disables at least the first cooling unit based completely or partially upon the patient's temperature.

In some embodiments, the controller controls a first rate of cooling of the first cooling unit and a second rate of cooling of the second cooling unit. In some of these embodiments, the first cooling unit further comprises a first compressor, a first condenser, and a first evaporator; and the second cooling unit further comprises a second compressor, a second condenser, and a second evaporator. The controller controls the first rate of cooling by controlling a first valve positioned between the first evaporator and the first compressor; and the controller controls the second rate of cooling by controlling a second valve positioned between the second evaporator and the second compressor.

A fan may be provided that blows ambient air on the first condenser, and the speed of the fan may be controlled by the controller.

In still other embodiments, the thermal control unit further includes an ambient air temperature sensor in communication with the controller. The controller selectively enables and disables the first cooling unit based at least partially upon a temperature sensed by the ambient air temperature sensor.

According to another embodiment of the present disclosure, a thermal control unit is provided that includes a housing; a cartridge; a second cooling unit; and a second controller. The cartridge is adapted to be removably positioned within the housing and includes a fluid outlet adapted to fluidly couple to a fluid supply line, a fluid inlet adapted to fluidly couple to a fluid return line, and a circulation channel coupled to the fluid outlet, the fluid inlet. The cartridge further includes a first cooling unit in thermal communication with the circulation channel and a first controller adapted to control the first cooling unit. The second cooling unit is positioned within the housing of the thermal control unit, but external to the cartridge. The second controller controls the second cooling unit and is adapted to communicate with the first cooling unit when the cartridge is positioned within the housing. The first and second controllers coordinate control of the first and second cooling units in order to control a temperature of a fluid in the circulation channel.

According to other aspects, the first cooling unit has a first heat transfer capacity and the second cooling unit has a second heat transfer capacity that is larger than the first heat transfer capacity.

The fluid circulates only inside the cartridge, even when the cartridge is inserted into the housing of the thermal control unit, in some embodiments.

According to another aspect, the first cooling unit comprises a first compressor, a first condenser, a first evaporator, and a first refrigerant. The second cooling unit comprises a second compressor, a second condenser, a second evaporator, and a second refrigerant. The first refrigerant is fluidly isolated from the second refrigerant when the cartridge is positioned within the housing.

A battery is included with the cartridge in some embodiments. The battery provides electrical power to the first cooling unit when the cartridge is removed from the housing. A plug is coupled to the housing and adapted to carry electrical power from a wall outlet to the housing to provide electrical power to the second cooling unit.

In some embodiments, the second controller is adapted to send instructions to the first controller instructing it to selectively enable and disable the first cooling unit based at least partially upon the temperature of the fluid.

According to another embodiment of the present disclosure, a thermal control unit for controlling a patient's temperature is provided. The thermal control unit includes a fluid outlet adapted to fluidly couple to a fluid supply line for delivering fluid to the patient; a fluid inlet adapted to fluidly couple to a fluid return line for receiving fluid returned from the patient; a fluid circulation channel coupled to the fluid outlet and the fluid inlet; a pump for circulating fluid through the fluid circulation channel from the fluid inlet to the fluid outlet; a first cooling unit; a fan; and a controller. The first cooling unit cools fluid circulating through the fluid circulation channel and includes a compressor, an evaporator, and a condenser. The fan is adapted to blow ambient air onto the condenser. The controller selectively controls a speed of the fan based at least upon a temperature of the circulating fluid.

According to other aspects, the thermal control unit also includes a pre-cooling unit positioned adjacent the fan and adapted to pre-cool the air blown onto the compressor by the fan. The controller diverts at least a portion of the fluid from the circulating fluid channel into the pre-cooling unit. The diverted fluid is used to pre-cool the air blown onto the compressor. The controller may control an amount of fluid diverted to the pre-cooling unit based at least partially upon a temperature of the patient.

In some embodiments, a second cooling unit is provided that is adapted to cool fluid circulating through the fluid circulation channel. The second cooling unit includes a second compressor, a second evaporator, and a second condenser. The controller may be adapted to change a first rate of cooling of the first cooling unit without changing a second rate of cooling of the second cooling unit, and vice versa. The controller may also, or alternatively, be adapted to disable the second cooling unit by ceasing circulation of a refrigerant through the second cooling unit, but by continuing to allow the pump to circulate fluid through the fluid circulation channel. Still further, the second cooling unit may be contained within a cartridge adapted to be removably positioned within a housing of the thermal control unit, and the first cooling unit may be contained within the housing outside of the cartridge.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
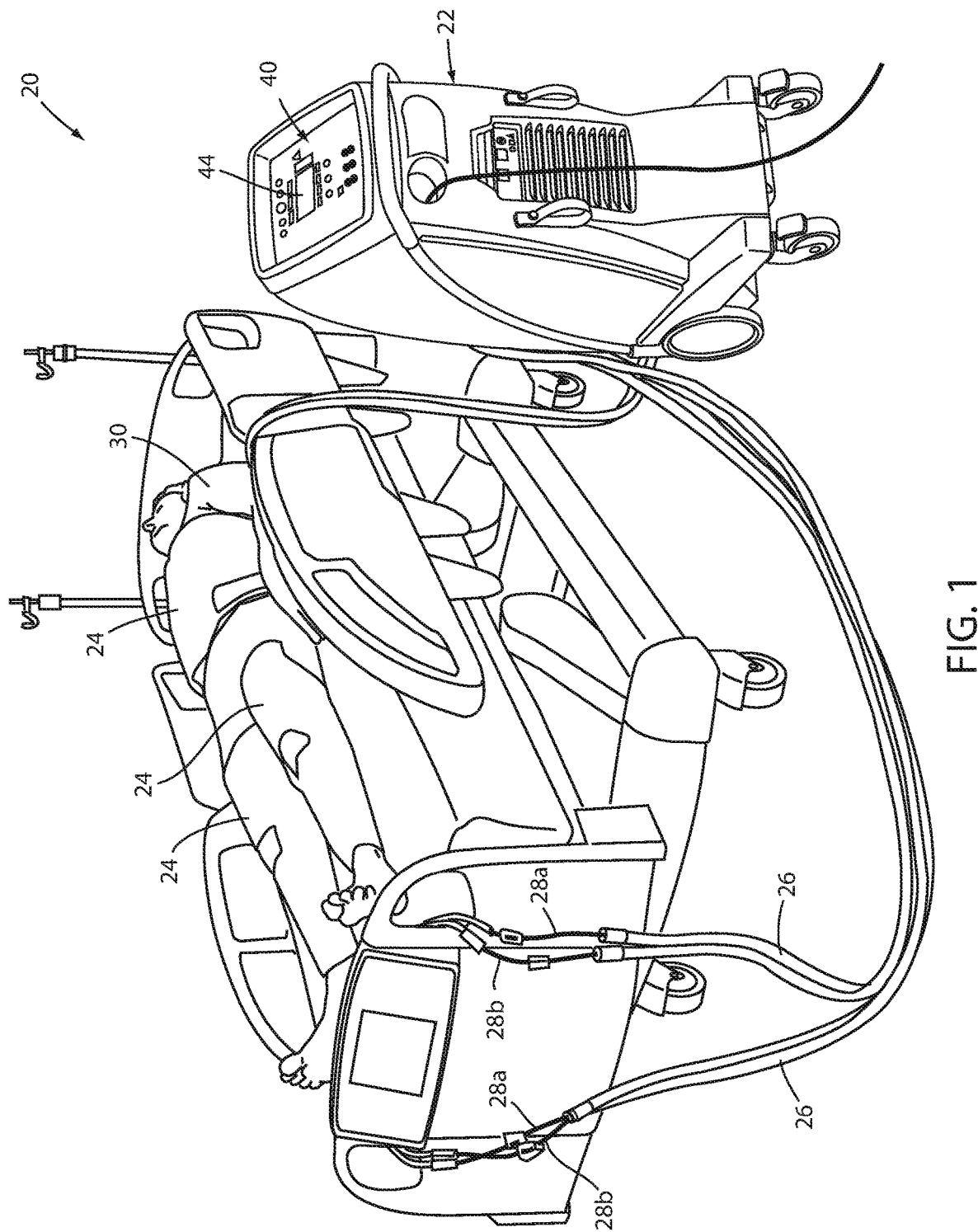
FIG. 1 is a perspective view of a thermal control system according to one aspect of the present disclosure shown applied to a patient on a patient support apparatus.

A thermal control system 20 according to one embodiment of the present disclosure is shown in FIG. 1. Thermal control system 20 is adapted to control the temperature of a patient 30, which may involve raising, lowering, or maintaining the patient's temperature, or combinations thereof. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, or other structure. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, etc.).

Thermal control unit 22 is coupled to thermal pads 24 via a plurality of hoses 26. Each hose includes one or more lines 28. In the embodiment shown in FIG. 1, each hose 26 includes a fluid supply line 28a and a fluid return line 28b. Thermal control unit 22 delivers temperature controlled fluid (such as, but not limited to, water) to the thermal pads 24 via the fluid supply lines 28a. After the temperature controlled fluid has passed through thermal pads 24, thermal control unit 22 receives the temperature controlled fluid back from thermal pads 24 via the return lines 28b.

In the embodiment of thermal control system 20 shown in FIG. 1, three thermal pads 24 are used in the treatment of patient 30. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply lines 28*a*, the temperature of the patient 30 can be controlled via the close contact of the pads 24 with the patient 30 and the resultant heat transfer therebetween.

Figure 2:
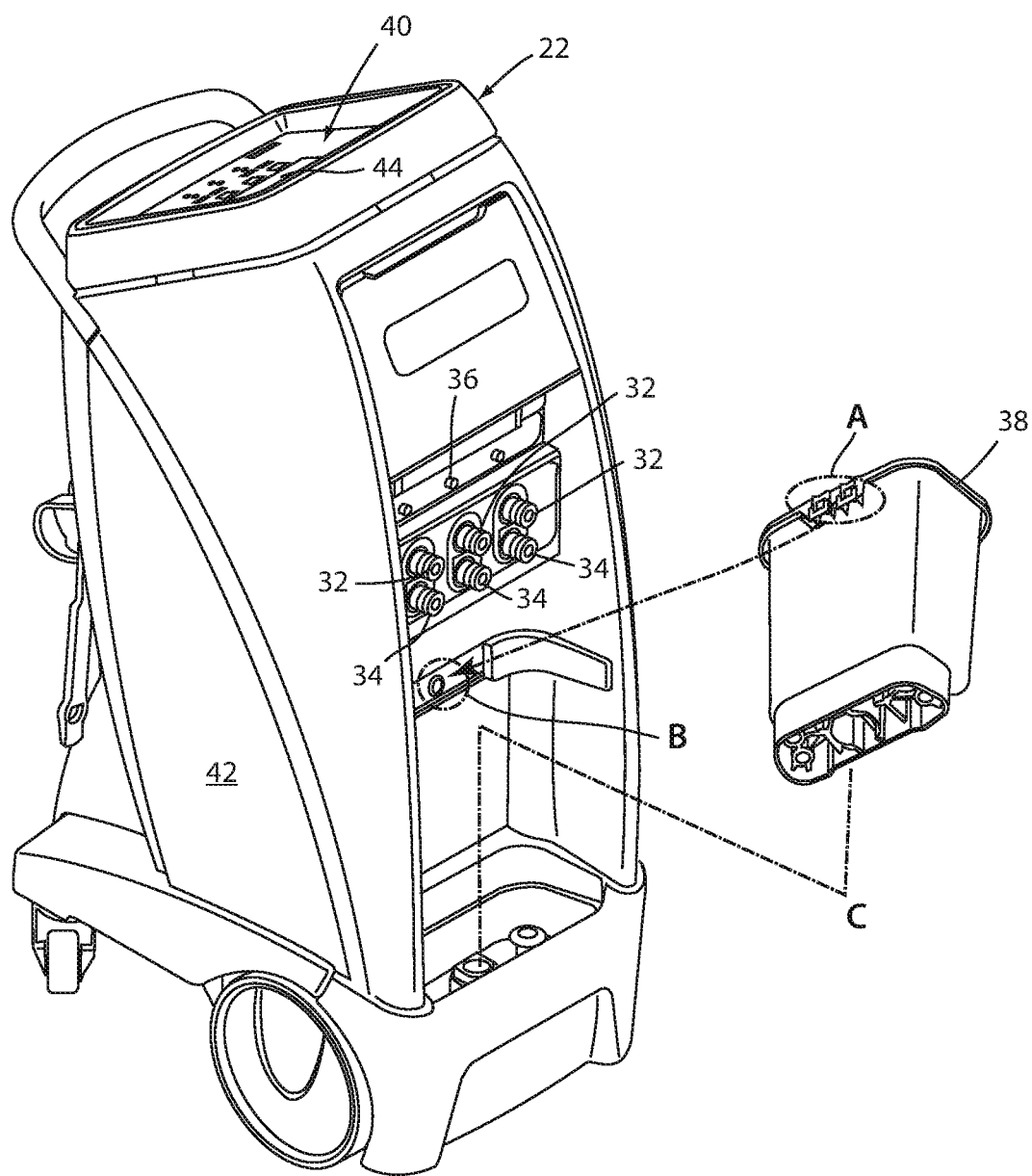
FIG. 2 is a perspective view of a thermal control unit of the thermal control system of FIG. 1.

As shown more clearly in FIG. 2, thermal control unit 22 includes a plurality of outlet ports 32, a plurality of inlet ports 34, at least one temperature probe port 36, and a removable reservoir 38. Outlet ports 32 are adapted to couple to one or more hoses 26 containing one or more supply lines 28*a*, while inlet ports 34 are adapted to couple to one or more hoses 26 containing one or more return lines 28*b*. In some embodiments, hoses 26 and ports 32 and 34 include conventional quick-connect fittings that enable the hoses 26 to be easily coupled to and decoupled from ports 32 and 34. Other types of fittings may be used.

Temperature probe port 36 is adapted to couple to a patient temperature probe that is used to sense the temperature of the patient. The patient temperature probe that is coupled to port 36 may be any suitable patient temperature probe that is able to sense the temperature of the patient at the location of the probe. In one embodiment, the patient temperature probe may be a conventional YSI 400 probes marketed by YSI Incorporated of Yellow Springs, Ohio, or a probe that is YSI 400 compliant. In other embodiments, different types of probes may be used with thermal control unit 22. Regardless of the specific type of patient temperature probe used, the temperature probe is connected to patient temperature probe port 36, which is in electrical communication with a controller inside of control unit 22. The controller, as will be discussed in greater detail below, is adapted, in at least some situations, to use the temperature sensed by at least one of the probes to control the temperature of the fluid circulated through control unit 22 and pads 24.

It will also be understood by those skilled in the art that the number of ports 32 and 34 can be varied to include either a smaller or a greater number than the three illustrated in FIG. 2. Still further, it will understood by those skilled in the art that the ports 32, 34 may be provided in various physical configurations and combinations to facilitate the connection and disconnection of the lines 28*a* and 28*b* and/or thermal pads 24. As but one example, instead of using a separate pair of ports 32 and 34 for each individual thermal pad 24, as shown in FIG. 1, it is possible to modify control unit 22 to include a single multi-tube outlet port 32 and a single multi-tube inlet port 34 that simultaneously couples and de-couples multiple sets of supply lines 28*a* and return lines 28*b* to and from control unit 22. Still other variations are possible.

As shown in FIGS. 1 and 2, thermal control unit 22 includes a user interface 40 positioned generally atop a housing 42 which houses the internal components of thermal control unit 22, as will be explained in greater detail below. User interface 40 of thermal control unit 22 includes, in the illustrated embodiment, a display 44 on which data, controls, and/or functions of the thermal control unit may be accessed. Such controls include one or more controls enabling a user to turn control unit 22 on and off, as well as one or more controls enabling the user to select a target temperature for the fluid delivered to thermal pads 24. In some embodiments, user interface 40 also allows a user to select a target temperature for the patient being treated, rather than a specific target temperature for the fluid. When this feature is present, thermal control unit 22 makes automatic adjustments to the temperature of the fluid in order to bring the patient's temperature to the desired patient target temperature.

Thermal control unit 22 is adapted, in the illustrated embodiment, to operate in a plurality of different modes that are selectable by a user. In a first mode, known as a manual mode, the thermal control unit 22 controls the temperature of the liquid circulating through control unit 22—and thereby the temperature of the fluid delivered to thermal pads 24—so that it matches a target temperature chosen by the user. In this mode, control unit 22 maintains the liquid at the chosen target temperature regardless of the patient's temperature, and control unit 22 may be used without any patient temperature probes, if desired. In a second mode, known as an automatic mode, the thermal control unit 22 controls the temperature of the liquid circulating through control unit 22 in such a manner that a target patient temperature is achieved and/or maintained. In this automatic mode, at least one patient temperature probe or sensor is coupled to patient temperature probe port 36 so that control unit 22 knows the patient's current temperature. In the automatic mode, control unit 22 does not necessarily adjust the temperature of the circulating fluid to maintain a constant temperature, but instead makes the necessary temperature adjustments to the fluid in order to reach, or maintain, the desired patient target temperature.

When the user has selected a target temperature for the fluid or a target temperature for the patient, thermal control unit 22 utilizes the selected target temperature, as well as the temperature readings from one or more internal sensors, to generate and send commands to an internal heat exchanger, as necessary, in order to cool and/or warm the fluid circulating through thermal control unit 22 and thermal pads 24 so that the selected target temperature is met. In at least one embodiment, thermal control unit 22 implements closed-loop feedback control of the heat exchanger using the output from the temperature sensor(s) such that the temperature of the circulating fluid is adjusted toward the target temperature. The closed loop feedback may take on multiple different forms, such as proportional-integral-derivative (PID) control, any variant thereof (e.g. proportional-integral (PI) control), or still other types of closed loop controls.

Figure 3:
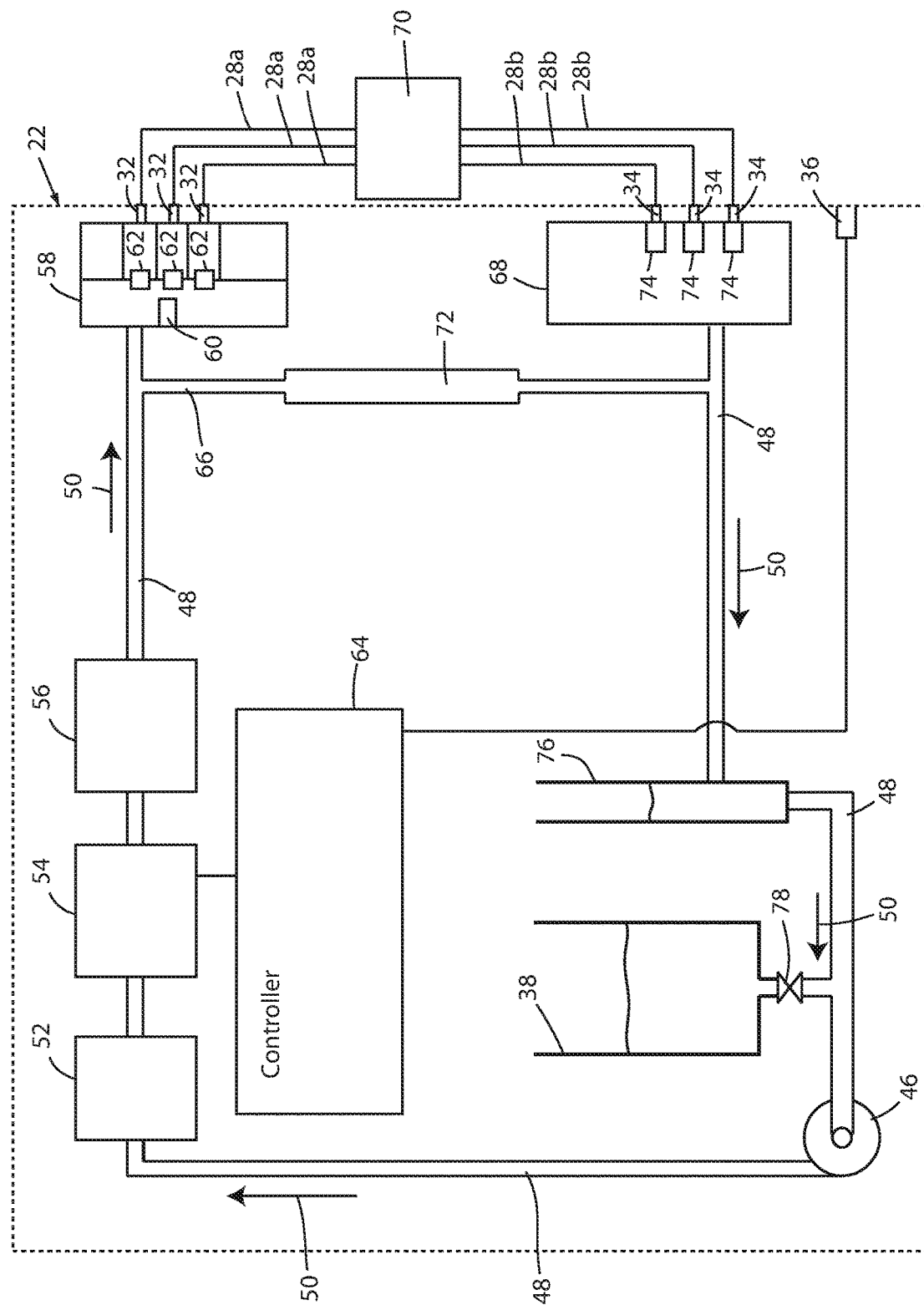
FIG. 3 is a block diagram of a control system for the thermal control unit of FIG. 2.

As shown in FIG. 3, thermal control unit 22 includes a pump 46 for circulating fluid through a circulation channel 48. Pump 46, when activated, circulates the fluid through circulation channel 48 in the direction of arrows 50 (clockwise in FIG. 3). Starting at pump 46 the circulating fluid first passes through a first cooling unit 52, followed by a second cooling unit 54, and then a heating unit 56. After exiting from heating unit 56, fluid in circulation channel 48 is delivered to an outlet manifold 58 having an outlet temperature sensor 60 and a plurality of valves 62. Outlet manifold 58 is also in fluid communication with outlet ports 32 and supplies fluid to the outlet ports 32 when the ports 32 are coupled to one or more hoses 26. In some embodiments, outlet valves 62 are omitted and temperatures sensor 60 may be positioned elsewhere along circulation channel 48.

Temperature sensor 60 is adapted to detect a temperature of the fluid inside of outlet manifold 58 and report it to a controller 64. Valves 62 are adapted to move between open and closed positions (and in some embodiments, one or more positions therebetween) under the control of controller 64. Valves 62 control how much fluid flows from outlet manifold 58 to each of the supply lines 28*a*, as will be discussed in greater detail below. Supply lines 28*a* are, in turn, coupled to a thermal load 70. Thermal load 70 in FIG. 3 refers to the one or more thermal pads 24 that are used to control the temperature of a patient 30.

Control unit 22 also includes a bypass line 66 fluidly coupled between a portion of circulation channel 48 just upstream of outlet manifold 58 and a portion of circulation channel 48 just downstream of an inlet manifold 68. Bypass line 66 allows fluid to circulate through circulation channel 48 even in the absence of any thermal pads 24 or lines 28a being coupled to any of outlet ports 32. In the illustrated embodiment, bypass line 66 includes an optional filter 72 that is adapted to filter the circulating fluid. If included, filter 72 may be a particle filter adapted to filter out particles within the circulating fluid that exceed a size threshold, or filter 72 may be a biological filter adapted to purify or sanitize the circulating fluid, or it may be a combination of both. In some embodiments, filter 72 is constructed and/or positioned within thermal control unit 22 in any of the manners disclosed in commonly assigned U.S. patent application Ser. No. 62/404,676 filed Oct. 11, 2016, by inventors Marko Kostic et al. and entitled THERMAL CONTROL SYSTEM, the complete disclosure of which is incorporated herein by reference.

Inlet manifold 68 is in fluid communication with inlet ports 34 that receive fluid returning from the one or more connected thermal pads 24. In the embodiment illustrated in FIG. 3, inlet manifold 68 further includes an inlet temperature sensor 74 associated with each inlet port 34. The temperature of the fluid returning from each inlet port 34 is therefore individually measurable. The outputs from the temperatures sensors 74 are fed to controller 64. In some embodiments, controller 64 displays these temperatures on display 44 of user interface 40, and/or uses these temperatures to control one or more of cooling units 52 and 54, and/or heating unit 56.

The incoming fluid from inlet ports 34, as well as the fluid passing through bypass line 66, travels back toward the pump 46 into an air separator 76. Air separator 76 is constructed to slow down the flow of fluid sufficiently to allow air bubbles contained within the circulating fluid to float upwardly and escape to the ambient surrounding. In some embodiments, air separator 76 is constructed in accordance with any of the configurations disclosed in commonly assigned U.S. patent application Ser. No. 62/361,124 filed Jul. 12, 2016, by inventor Gregory S. Taylor and entitled THERMAL CONTROL SYSTEM, the complete disclosure of which is hereby incorporated herein by reference. After passing through air separator 76, the circulating fluid flows past a valve 78 positioned beneath fluid reservoir 38 that supplies fluid to thermal control unit 22. After passing by valve 78, the circulating fluid travels to pump 46 and the fluid circuit is repeated.

Controller 64 of thermal control unit 22 is contained within the housing 42 of thermal control unit 22 and is in electrical communication with a variety of different sensors and/or actuators, such as pump 46, first and second cooling units 52 and 54, heating unit 56, user interface 40, outlet temperature sensor 60, valves 62, inlet temperature sensors 74, and patient temperature probe port 36. Controller 64 includes any and all electrical circuitry and components necessary to carry out the functions and algorithms described herein, as would be known to one of ordinary skill in the art. Generally speaking, controller 64 may include one or more microcontrollers, microprocessors, and/or other programmable electronics that are programmed to carry out the functions described herein. It will be understood that controller 64 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions inside thermal control unit 22, or they may reside in a common location within thermal control unit 22, or they may include portions that are outside thermal control unit 22. When physically distributed, the components may communicate using any suitable serial or parallel communication protocol, such as, but not limited to, CAN, LIN, Firewire, I-squared-C, RS-232, RS-485, universal serial bus (USB), etc.

Thermal control unit 22 may also be modified to include one or more flow sensors that measure the rate of fluid flow and report this information to controller 64. In such modified embodiments, controller 64 uses the flow rate in determining what control signals to send to cooling units 52 and 54, heating unit 56, valves 62, pump 46, and/or other components of thermal control unit 22.

It will be understood by those skilled in the art that the particular order of the components along circulation channel 48 of control unit 22 may be varied from what is shown in FIG. 3. For example, although FIG. 3 depicts pump 46 as being upstream of cooling and heating units 52, 54, and 56, and also depicts air separator 76 as being downstream of bypass line 66, this order may be changed. Air separator 76, pump 46, cooling and heating units 52, 54, and/or 56 may be positioned at any suitable location along circulation channel 48. Further, in some embodiments, reservoir 38 is moved so as to be in line with and part of circulation channel 48, rather than external to circulation channel 48 as shown in FIG. 3, thereby forcing the circulating fluid to flow through reservoir 38 rather than around reservoir 38.

Figure 4:
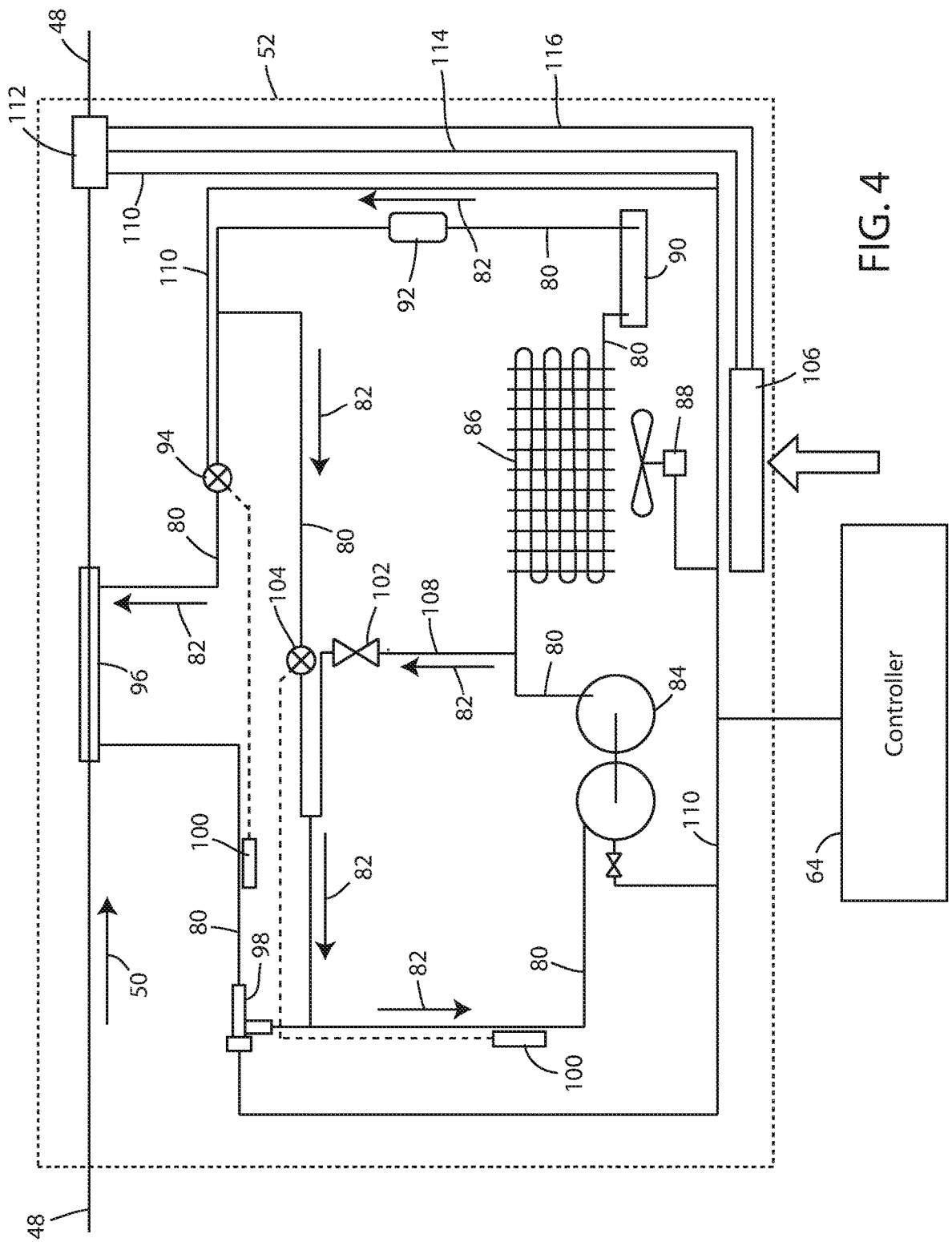
FIG. 4 is a block diagram of one embodiment of a cooling unit usable in the thermal control unit of FIG. 2.

FIG. 4 depicts in greater detail an illustrative construction of first cooling unit 52. It will be understood that second cooling unit 54 is constructed in an identical manner, in at least some embodiments, and therefore will not be described separately. First cooling unit 52 includes a refrigerant circulation channel 80 through which a conventional refrigerant circulates in the direction indicated by arrows 82. First cooling unit 52 further includes a compressor 84, a condenser 86, a fan 88, a refrigerant receiver 90, a refrigerant filter/dryer 92, a main expansion valve 94, an evaporator/heat exchanger 96, a suction pressure control valve 98, and a pair of temperature sensing bulbs 100. First cooling unit 52 further includes a bypass valve 102, a desuperheating valve 104, and a pre-cooling unit 106.

As fluid flows through circulation channel 48 of thermal control unit 22, it comes into thermal contact with evaporator/heat exchanger 96. Inside evaporator/heat exchanger 96, the refrigerant is expanding to a gas phase and absorbing heat from its surrounding environment, including the circulating fluid passing through circulation channel 48. Evaporator/heat exchanger 96 therefore cools the circulating fluid of circulation channel 48 as it passes by evaporator/heat exchanger 96. After passing through evaporator/heat exchanger 96, the heated (from the circulating fluid of channel 48) refrigerant passes through suction pressure control valve 98 to compressor 84. Compressor 84 forces the refrigerant through condenser 86 where it then passes through receiver 90, filter/dryer 92, main expansion valve 94, and back to evaporator/heat exchanger 96. When passing through condenser 86, the refrigerant is compressed and changed from a vapor state to a liquid state, thereby releasing heat to the ambient atmosphere. This removal of this heat from the refrigerant while passing through condenser 86 is facilitated by fan 88, which blows ambient air over the condenser 86 in order to carry away the heat released from the refrigerant.

In one embodiment of first cooling unit 52, compressor 84 is a variable speed compressor whose speed is controlled by controller 64. By controlling the speed of compressor 84, controller 64 is able to adjust the level of heat removal that takes place as the fluid of circulation channel 48 passes through evaporator/heat exchanger 96. Controller 64 controls the speed of compressor 84, in at least one embodiment, based upon a temperature of the patient, as detected by a patient temperature probe whose output is fed into patient temperature probe port 36. Controller 64 may also, in some embodiments, control the speed of compressor 84 based upon the temperature of the circulating fluid, such as detected by outlet temperature sensor 60 and/or inlet temperature sensors 74. Still further, in some embodiments, controller 64 controls the speed of compressor 84 based upon the rate at which the patient's temperature is changing.

In one embodiment, controller 64 reduces the speed of compressor 84 if any one or more of the following conditions occur: (1) the patient's measured temperature is below the patient's target temperature; (2) the patient's temperature is dropping faster than a desired cooling rate; (3) the fluid temperature is colder than the patient's temperature by more than a threshold difference; and (4) the fluid temperature is colder than an absolute threshold. For any of these conditions, the temperature of the circulating fluid being delivered to the thermal pads 24 is undesirably cold, so controller 64 reduces the speed of compressor 84, thereby reducing the rate at which heat is removed from the circulating fluid. This reduced speed of compressor 84 continues until the condition(s) that caused the reduced speed end. If any of the opposite of the aforementioned conditions occur, controller 64 may be programmed to increase the speed of compressor 84.

By including a variable speed compressor 84, the efficiency of thermal control unit 22 can be increased relative to conventional thermal control units. Further, the noise of thermal control unit 22 can be reduced relative to conventional thermal control units. With respect to efficiency, conventional thermal control units often include a fixed speed compressor that delivers a fixed amount of cooling power (i.e. removes heat from the circulating fluid at a substantially fixed rate). If the delivered cooling power is greater than is needed to cool the circulating fluid in circulation channel 48, the compressor is either shut off (disabled), or the extra cooling power is diverted. The diversion of the extra cooling power can be accomplished by sending a portion of the compressed refrigerant through a hot gas bypass 108. Hot gas bypass diverts refrigerant from evaporator/heat exchanger 96. This diversion is controlled by bypass valve 102, which is under the control of controller 64. This diversion, however, is inefficient, as the extra cooling power that arises from running the compressor 84 at a fixed speed greater than the current cooling needs is wasted on pumping the refrigerant through bypass 108.

In addition to its energy inefficiency, another undesirable feature of many prior art thermal control units is noise. By continuing to run a compressor at a speed that is greater than necessary to achieve the currently desired cooling power, the compressor makes more noise than is necessary. This may be undesirable to either or both of the caregiver operating the thermal control unit 22 and the patient whose temperature is being controlled by thermal control unit 22.

Although compressor 84 is a conventional variable speed compressor in one embodiment, even conventional variable speed compressors 84 typically include a minimum speed. If that minimum speed results in a greater cooling power than necessary (i.e. more heat removal from the fluid circulating in circulation channel 48 than is necessary), then compressor 84 can be either shut off (disabled) or refrigerant can be diverted to bypass 108. Alternatively, or additionally, controller 64 can be programmed to turn on heating unit 56 to increase the temperature of the circulating fluid to a desired temperature.

In at least one embodiment of thermal control unit 22, controller 64 is programmed to also control the speed of fan 88 such that the amount of cooling power delivered by first cooling unit 52 can be varied beyond the limits of the variable speed range of variable speed compressor 84. In this embodiment, if less cooling power is needed from thermal control unit 22 at a particular time than can be achieved by reducing the speed of compressor 84 to its lowest speed, controller 64 is programmed to reduce the speed of fan 88. The reduction in the speed of fan 88 decreases the thermal transfer efficiency of condenser 86, thereby removing less heat from the refrigerant as it passes through condenser 86. This has the effect of reducing the cooling power delivered by first cooling unit 52 even further than what is obtainable by merely slowing compressor 84 to its lowest speed. If even less cooling power is needed, controller 64 is programmed in some embodiments to completely shut off fan 88. If this cessation of fan 88 and the reduction in speed of compressor 84 to its lowest speed still results in excess cooling power, controller 64 is programmed to either stop compressor 84 and/or divert a controlled amount of the refrigerant to bypass 108.

As an alternative and/or an addition to the speed control of both compressor 84 and fan 88, controller 64 is also programmed in some embodiments to utilize pre-cooling unit 106 in situations where the amount of cooling delivered by first cooling unit 52 exceeds the required level of cooling. Controller 64 is in communication with a communications bus 110 that is coupled to suction pressure control valve 98, compressor 84, fan 88, main expansion valve 94, and a pre-cooling valve 112. Communications bus 110 allow controller 64 to communicate with each of these devices. In alternative embodiments, bus 110 is partially or wholly replaced with individual connections between controller 64 and one or more of these devices. Although not shown in FIG. 4, temperature sensing bulbs 100 may also be coupled to bus 110 in order to communicate with controller 64, or they may communicate using dedicated channels.

Pre-cooling valve 112 is fluidly coupled to circulating channel 48, a pre-cooling supply line 114, and a pre-cooling return line 116. When controller 64 determines that first cooling unit 52 (and/or second cooling unit 54) are cooling the fluid in circulating channel 48 more than is necessary to carry out the desired thermal treatment of the patient, controller 64 diverts all or a portion of the fluid in circulating channel 48 down pre-cooling supply line 114 where the fluid travels to pre-cooling unit 106. Pre-cooling unit 106 is placed in the path of the air stream that flows over condenser 86 when fan 88 is turned on. Pre-cooling unit 106 is constructed in any suitable manner so as to pre-cool the air delivered by fan 88 to condenser 86. This pre-cooled air has the effect of increasing the efficiency of heat transfer between condenser 86 and the ambient air being blown over condenser 86. As a result, controller 64 reduces the speed of fan 88, thereby reducing the noise of first cooling unit 52 further.

After the fluid from supply line 114 passes through pre-cooling unit 106, it returns to circulation channel 48 via pre-cooling return line 116. Once back in circulation channel 48, the fluid passes into second cooling unit 54 and the components downstream thereof.

As was noted previously, thermal control unit 22 includes a second cooling unit 54. Second cooling unit 54 is constructed in the same manner as first cooling unit 52, in at least some embodiments. In other embodiments, second cooling unit 54 is constructed in the same manner but includes a fixed speed compressor, rather than a variable speed compressor. Second cooling unit 54 also differs from first cooling unit 52, in at least some embodiments, by having a different maximum cooling power than first cooling unit 52. That is, in some embodiments, first cooling unit 52 has a maximum cooling power of X watts and second cooling unit 54 has a maximum cooling power of Y watts, and X and Y are different values. Second cooling unit 54 may utilize a refrigerant that is fluidly isolated from the refrigerant used in first cooling unit 52.

When first and second cooling units 52 and 54 have different maximum cooling powers, controller 64 is programmed to utilize both cooling units 52 and 54 when the needed cooling power exceeds one or both of their maximum cooling powers, and to shut off one of the cooling units when less than cooling power is needed than the maximum cooling power of at least one of the units. In some embodiments, controller 64 is programmed to automatically initially turn on (i.e. enable) both cooling units 52 and 54 when a temperature management session begins, leave both of the cooling units 52 and 54 on while the patient's temperature is adjusted to a desired target temperature, and then shut off one of the cooling units 52 or 54 after the target temperature is reached. In such embodiments, it is typically unnecessary for both cooling units 52 and 54 to operate in order to maintain the patient's temperature at the target temperature.

In other embodiments, controller 64 is programmed to periodically and/or intermittently calculate whether the cooling power of both cooling units 52 and 54 is needed and, if not, shut down whichever one of the cooling units is not needed. In such embodiments, controller 64 accesses a memory contained within thermal control unit 22 that contains data regarding the respective maximum cooling powers of each of the cooling units 52 and 54. Controller 64 selects whichever cooling unit (52 or 54) has a sufficient maximum cooling power to meet the current cooling needs of thermal control unit 22. If both of the cooling units are individually able to meet the current cooling demands, controller 64 shuts down the cooling unit with the greater cooling capacity, in at least some embodiments. In other embodiments, controller 64 may be programmed to shut down the cooling unit 52 or 54 that uses more energy, or that has greater noise output, or to make a decision that is based on a combination of these and other factors. The noise data may be gathered empirically from each of the cooling units 52 and 54 and stored in a memory on board thermal control unit 22 that is accessible to controller 64.

Still further, in some embodiments, controller 64 is programmed to allow a user to select which cooling unit 52 and 54 to use in situations where both of the cooling units are not needed. Additionally or alternatively, controller 64 may be programmed to select which cooling unit 52, 54 to use (when both are not needed) based on how long each cooling unit has been used in the past (cumulative time of use and/or number of cycles and/or other usage metric) and/or on any measurable decrease in performance of one cooling unit versus the other over time.

In some embodiments where controller 64 is programmed to periodically or intermittently calculate how much cooling power thermal control unit 22 needs to generate, controller 64 may be programmed to compare the temperature of the fluid in outlet manifold 58 to the temperature of the fluid in inlet manifold 68. Using this temperature difference and the flow rate of the fluid exiting from and returning to thermal control unit 22, controller 64 calculates how much thermal energy is being added to the circulating fluid from the time the fluid exits thermal control unit 22 (via outlet ports 32) till the time the fluid returns to thermal control unit (via inlet ports 34). Controller 64 then compares this rate of thermal energy addition to the cooling powers of cooling units 52 and 54. If the rate of heat addition is less than the maximum cooling rates of either of the cooling units 52 and 54, controller 64 may shut down one of the cooling units 52, and/or take other action as discussed above.

Controller 64 may also be programmed to take into account not just the current temperature of the fluid exiting from outlet manifold 58 via ports 32 when calculating the cooling demands of thermal control unit 22, but also the target temperature or an anticipated target temperature of the fluid exiting from outlet manifold 58. Thus, for example, controller 64 may be in the process of lowering the temperature of the fluid exiting outlet manifold 58 to a target temperature, in which case controller 64 calculates how much more energy must be removed from the circulating fluid in order to bring the temperature of the fluid at outlet manifold 58 to the desired target temperature. Alternatively, or additionally, controller 64 may be operating in a mode where thermal control unit 22 is controlling the rate at which a patient's temperature is cooled and, although the fluid inside outlet manifold 58 may be at its current target temperature, controller 64 is going to decrease that target temperature in order to ensure that the patient's cooling rate matches the desired cooling rate. The patient's current temperature and/or target temperature may therefore also be a factor in calculating the current or future cooling demands of thermal control unit 22. Still other factors may be used in calculating how much cooling power thermal control unit 22 should currently maintain or provide in the near future.

As an alternative to shutting down one of cooling units 52 or 54 when one of them is not needed, controller 64 is programmed in still other embodiments to take other actions. These other actions include decreasing the speed of the fan 88 in either or both of the cooling units, decreasing the speed of the variable speed compressor in first cooling unit 52 (and/or second cooling unit 54 if it includes a variable speed compressor), and diverting some of the circulating fluid to pre-cooling unit 106 of first cooling unit 52 (and/or diverting circulating fluid to a pre-cooling unit 106 of second cooling unit 54 if second cooling unit 54 includes such a pre-cooling unit 106). Thus, controller 64 is programmed in some embodiments to split the required cooling load between the two cooling units 52 and 54 and/or to separately control the rates of cooling of each of the first and second cooling units 52 and 54. The splitting may be equal or it may be unequal. Further, the manner in which the cooling load is split may be continually and/or repetitively adjusted based on the patient temperature, circulating fluid temperature, target temperature, and other factors. Thus, the rates of cooling of each of the cooling units 52 and 54 may be individually changed throughout the patient's thermal therapy session.

In those cases where controller 64 splits the cooling load between first and second cooling units 52 and 54, controller 64 may programmed to divide the cooling load in such a way that neither cooling unit 52 or 54 is directed to provide less cooling power than a predetermined minimum associated with each cooling unit 52 and 54. The predetermined minimums may be different for each cooling unit 52 and 54. In some embodiments, the predetermined minimums are based on the minimum cooling power of a cooling unit (52 or 54) when the compressor of that cooling unit is operating at its minimum speed; when the fan 88 is operating at its minimum speed (or stopped); when no refrigerant is being fed to bypass 108; when the cooling unit is operating at a desired level of efficiency; and/or when the cooling unit is operating at or below a desired noise level. In this manner, controller 64 is able to control the cooling units 52 and 54 in a manner that improves the overall efficiency and/or noise level of thermal control unit 22.

In some embodiments, one or both of the cooling units 52 and 54 further includes an ambient air sensor that is positioned adjacent condenser 86 and that measures the temperature of the ambient air that is blown by fan 88 over condenser 86. Controller 64 uses this temperature measurement to adjust the cooling powers associated with each cooling unit 52 and 54. That is, the ability of each cooling unit 52 and 54 to cool down the circulating fluid changes depending upon the ambient air temperature. When the ambient air temperature is relatively warm, the cooling units must work harder to provide a desired level of cooling than when the air is relatively cool. Controller 64 is programmed in some embodiments to take into account this temperature level when deciding whether to shut down a cooling unit and/or when deciding how to allocate how much cooling each cooling unit is to carry out.

It will be understood that, although controller 64 has been primarily described herein as changing the rate of cooling provided by the cooling units 52 and 54 by changing the condenser speed, fan speed, and/or pre-cooling valve 112, controller 64 also communicates with and controls main expansion valve 94 and suction pressure control valve 98 in order to change the amount of cooling provided by the cooling unit. That is, as more refrigerant is allowed into evaporator 96, evaporator 96 is able to absorb more heat from the fluid inside circulation channel 48. Controller 64 controls the amount of refrigerant flowing to evaporator 96 via suction valve 98 and main expansion valve 94. In one embodiment, controller 64 varies the refrigerant flow by controlling suction valve 98, which is positioned between the evaporator 96 and the compressor 84. Controller 64 varies the opening and closing of valve 98 in order to match the varying cooling needs of the fluid circulating in circulation channel 48.

In some embodiments of thermal control unit 22, one or both of the cooling units 52 or 54 are modified from what is shown in FIG. 4. Such modifications may vary. In one such modified embodiment, no bypass 108 is included in the cooling unit. Instead, all of the refrigerant is pumped through condenser 86 and controller 64 takes other measures in situations where the cooling unit 52 or 54 is producing more cooling power than is currently needed. These additional measures include reducing the speed of fan 88, reducing the speed of the compressor (if it is a variable speed compressor), diverting fluid to pre-cooling unit 106, decreasing the cooling power currently being generated by the other cooling unit, and/or shutting down the cooling unit. Other modifications include, but are not limited to, omitting pre-cooling unit 106, using a fixed speed fan 88, changing the valving arrangement (e.g. valves 94, 104, and/or 98), and others.

Still another modification to one or both of cooling units 52 and 54 is the removal of one or more of valves 94, 98, and 102. When one or more of these valves is removed, controller 64 controls the amount of heat withdrawn from the fluid inside of circulation channel 48 by controlling the speed of compressor 84, the speed of fan 88, the diversion of fluid via pre-cooling valve 112 (if present), and/or the shutting down of compressor 84.

It will be understood that when one or both of cooling units 52 or 54 is shut down (i.e. its compressor is shut down), circulating fluid continues to flow through channel 48. Thus, for example, if first cooling unit 52 has its compressor shut off but second cooling unit 54 has its compressor still operating so that refrigerant is pumped to its evaporator 96, the fluid circulating within circulation channel 48 will still continue to circulate past both the evaporators 96 of both the first and second cooling units 52 and 54. The same is true if first cooling unit 52 is operating but second cooling unit 54 is shut down.

Still other modifications that may be made to thermal control unit 22 include the following: splitting circulation channel 48 into separate branches so that circulating fluid passes through first and second cooling units 52 and 54 in parallel, rather than in the serial fashion shown in FIG. 3; omitting one of the cooling units 52 or 54; omitting heating unit 56; selectively feeding the heated exhaust air from fan 88 after it has passed through condenser 86 to heating unit 56 so that heating unit 56 is able to operate while consuming less energy; and/or selectively feeding the heated exhaust air from fan 88 after it has passed through condenser 86 to another portion of circulation channel 48 when fine-tuned temperature increases are desired in the circulating fluid.

Figure 5:
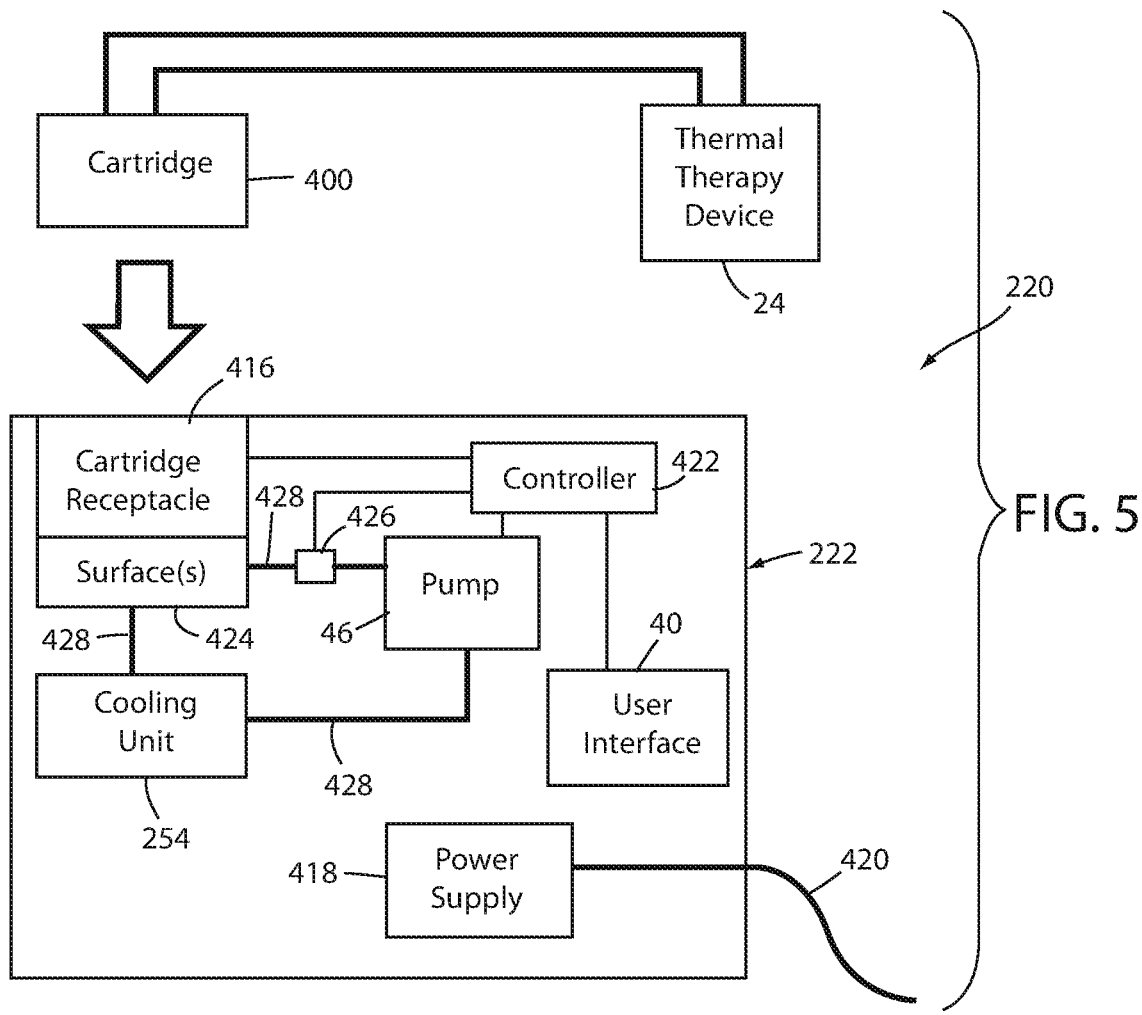
FIG. 5 is a block diagram of another thermal control system according to a second embodiment of the present disclosure.
Figure 6:
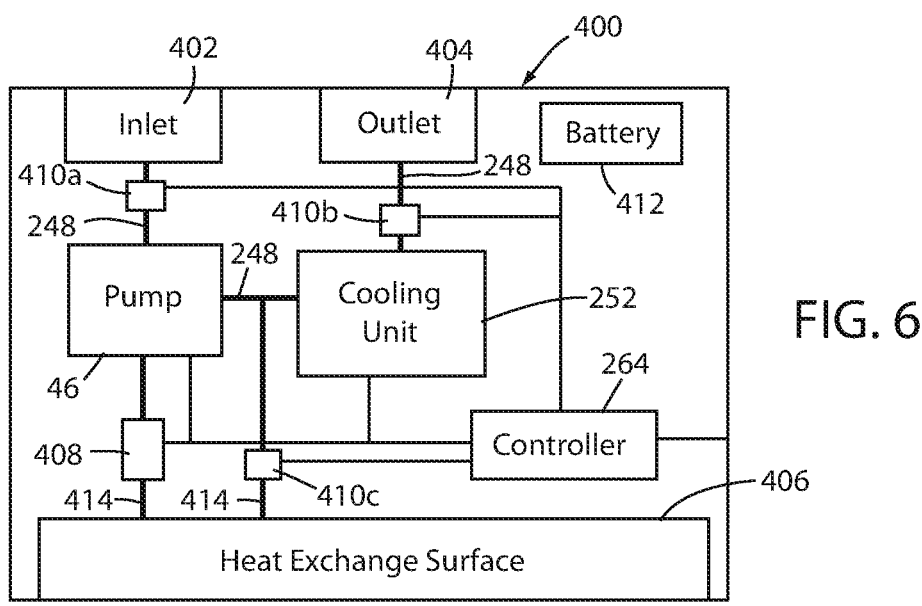
FIG. 6 is a block diagram of a cartridge usable in the thermal control system of FIG. 5.

FIGS. 5 and 6 illustrate an alternative embodiment of a control system 220 according to another aspect of the present disclosure. Control system 220 includes a number of components common to control system 20, as well as a number of components that are new or modified. Those components of control system 220 that are the same as components of control system 20 have been given the same reference number, and unless otherwise explicitly described below, operate in the same manner as described above with respect to control system 20. Those components of control system 220 that have been modified from corresponding components of control system 20 have been given the same reference number increased by two hundred. Those components that are new to system 220 have been given a new reference number.

Control system 220 differs primarily from control system 20 in that thermal control unit 222 is adapted to releasably receive a cartridge 400. Cartridge 400 includes one or more inlets 402 and one or more outlets 404 that are adapted to releasably couple to a fluid supply line 28a and a fluid return line 28b. Inlets 402 and outlets 404 may be constructed in the same manner as inlet ports 34 and outlet ports 32 of thermal control unit 22. Fluid lines 28a and 28b couple to one or more thermal pads 24 used in the thermal treatment of a patient.

As shown in FIG. 6, cartridge 400 includes a pump 46, a cooling unit 252, one or more heat exchange surfaces 406, a valve 408, a plurality of temperature sensors 410a, b, and c, a controller 264, and a battery 412. Inlet 402, outlet 404, pump 46, and cooling unit 252 are fluidly coupled together by a circulation channel 248. Circulation channel 248 also includes an auxiliary channel 414 that couples circulation channel 248 to heat exchange surface 406. Fluid is selectively allowed to flow to heat exchange surface 406 when valve 408 is opened. When valve 408 is closed, fluid remains inside circulation channel 248 and is pumped therethrough without traveling through auxiliary channel 414 to heat exchange surface 406. Valve 408 therefore controls whether the fluid circulating inside of cartridge 400—and how much of that fluid—comes into contact with the heat exchange surface 406 or not. As will be explained in more detail below, valve 408 is generally closed when cartridge 400 is positioned outside of thermal control unit 222 and is generally opened when cartridge 400 is inserted into thermal control unit 222.

Although not illustrated in FIG. 6, cartridge 400 may include a user interface adapted to allow a user to select a desired temperature for the fluid exiting outlet 404. Alternatively or additionally, cartridge 400 may include one or more patient temperature probe ports, such as patient temperature probe port 36 of thermal control unit 22. Such ports, if included, are adapted couple to a temperature probe that measures a temperature of a patient undergoing thermal treatment. Still further, cartridge 400 may be modified to include one or more heating units in order to heat the fluid circulating in circulation channel 248, thereby allowing cartridge 400 to providing warming thermal treatment and/or finer control of the temperature of the fluid exiting outlet 404.

Still further modifications are possible to cartridge 400, such as, but not limited to, the addition of a fluid reservoir that enables cartridge 400 to store a volume of fluid greater than the volume of circulation channel 248. In other embodiments, cartridge 400 may be modified to include one or more vacuum chambers to provide quick cooling to a volume of the circulating fluid. An example of one such vacuum chamber that can be incorporated into cartridge 400 is disclosed in commonly assigned U.S. patent application Ser. No. 62/311,054 filed Mar. 21, 2016, by inventor Gregory Taylor and entitled MOBILE THERMAL SYSTEM, the complete disclosure of which is incorporated herein by reference. In still other modified embodiments, cartridge 400 may be constructed in a hinged manner, such as any of the manners disclosed in commonly assigned U.S. patent application Ser. No. 62/451,121 filed Jan. 27, 2017, by inventors Martin Stryker et al. and entitled THERMAL CONTROL SYSTEM WITH FLUID CARTRIDGES, the complete disclosure of which is also hereby incorporated herein by reference. Still other modifications may be made to cartridge 400.

Controller 264 operates in a similar manner to controller 64 of thermal control unit 22. That is, controller 264 is adapted to control pump 46 and cooling unit 252 in a manner that adjusts the temperature of the fluid exiting outlet 404 toward a desired target temperature, maintains the temperature of the fluid at a target temperature, and/or that otherwise serves to control the temperature of a patient in a desired manner. In carrying out this control, controller 264 utilizes the temperature readings from one or more of the temperatures sensors 410a, b, and c. When cartridge 400 is decoupled from thermal control unit 222, controller 264 does not utilize the temperature readings from temperature sensor 410c because, as mentioned above, valve 408 is generally closed when cartridge 400 is decoupled from thermal control unit 222, and therefore no fluid is typically flowing past temperature sensors 410c.

Cartridge 400 is adapted, in at least one embodiment, to provide stand-alone temperature management for a patient. Cartridge 400 is therefore able to control the temperature of a fluid delivered via outlet 404 to one or more thermal pads 24 and returned back to cartridge 400 via inlet 402. When cartridge 400 is operating in a stand-alone mode, controller 264 operates cooling unit 252 in a manner that provides all of the cooling power needed to cool thermal pads 24 to a desired temperature. Cooling unit 252 may be constructed in the same manner as cooling unit 52 of system 20, or it may be modified in any of the manners discussed above with respect to cooling unit 52. Alternatively, cooling unit 252 may be a thermoelectric cooling unit, or utilize another type of cooling technology that is more compact than the vapor-compression cycle technology of cooling unit 52.

Cartridge 400 is adapted to be inserted into a cartridge receptacle 416 of thermal control unit 222 (FIG. 5). When inserted into receptacle 416, thermal control unit 222 is adapted to provide additional heating and/or cooling capabilities to cartridge 400. This enables quicker heating and/or cooling of the fluid that circulates through circulation channel 248 of cartridge 400. This also enables thermal treatment of a patient to continue with cartridge 400 even in situations where the battery 412 of cartridge 400 has been drained. This continued treatment is possible because thermal control unit 222 includes its own power supply 418 and this power supply is large enough to power both thermal control unit 222 and cartridge 400. As shown in FIG. 5, thermal control unit 222 is designed in at least some embodiments to include an electrical cord 420 having a plug on its free end (not shown) that can be plugged into a conventional electrical wall outlet in order to receive electrical power from a mains supply. Power supply 418 rectifies, conditions, and/or filters the electrical power delivered by cord 420 to the appropriate voltages needed for the various components of thermal control unit 222 and cartridge 400. In some embodiments, thermal control unit 222 may also include a rechargeable battery that can be used in situations where an electrical outlet may not be nearby.

In some embodiments, thermal control unit 222 is modified to include an energy transfer device that electrically couples with cartridge 400 when cartridge 400 is inserted into receptacle 416. The energy transfer device supplies electricity to cartridge 400. This electricity may be used by cartridge 400 to recharge battery 412 and/or to power the electrical components of cartridge 400. The energy transfer device used to supply the electrical power to cartridge 400 may be a wireless energy transfer device that utilizes one or more coils for inductively transferring power to cartridge 400, or it may be a conductive transfer device that includes physical contact with one or more conductors on cartridge 400. In some embodiments, the energy transfer device also carries out communications between cartridge 400 and thermal control unit 222. More specifically, such communication includes communications between controller 264 of cartridge 400 and a controller 422 of thermal control unit 222. In those embodiments where the power and data transfer is carried out wirelessly, the power and data may be transferred using any of the devices and methods disclosed in commonly assigned U.S. Pat. No. 9,289,336 issued Mar. 22, 2016, to inventors Clifford Lambarth et al. and entitled PATIENT SUPPORT WITH ENERGY TRANSFER, the complete disclosure of which is incorporated herein by reference. Still other types of data and/or energy transfer devices may be used.

When cartridge 400 is inserted into receptacle 416 of thermal control unit 222, thermal control unit 222 is able to add to the cooling power of cartridge 400 by having cooled fluid come into contact with one or more heat exchange surfaces 424. Heat exchange surfaces 424 are positioned and oriented such that they come into physical contact with one or more of the heat exchange surfaces 406 of cartridge 400 when cartridge 400 is inserted into receptacle 416 of thermal control unit 222. As a result, when thermal control unit 222 delivers cooled fluid to surfaces 424, and controller 264 of cartridge 400 has opened valve 408 such that fluid inside of cartridge 400 is flowing into contact with heat exchange surface 406 of cartridge 400, the cooling of heat exchange surface 424 removes heat from heat exchange surface 406, which in turn removes heat from the fluid circulating inside of cartridge 400. In such situations, the fluid circulating inside of cartridge 400 has its heat removed twice: first when it passes over heat exchange surface 406 and second when it passes through cooling unit 252. The coupling of cartridge of 400 to thermal control unit 222 therefore enables greater rates of heat removal from the circulating fluid inside of cartridge 400, which in turn allows a patient to be cooled quicker.

Temperature-controlled fluid is delivered to surfaces 424 by pumping a fluid—such as, but not limited to, water—through a fluid circulation channel 428 that fluidly couples together pump 46, cooling unit 254, and surfaces 424. Circulation channel 428 forms a closed circuit for fluid flow. Thus, pump 46 pumps fluid to cooling unit 254 where the fluid is cooled. After passing through cooling unit 254, the fluid flows into physical contact with the one or more surfaces 424. After passing over surfaces 424, the fluid returns to pump 46, and the circuit repeats. In at least one embodiment, the fluid circulating inside of circulation channel 428 remains physically separated from the fluid inside of cartridge 400 that is pumped to thermal pads 24, even when cartridge 400 is inserted into receptacle 416 of thermal control unit 222. Thus, the fluid inside of thermal control unit 222 is used to cool surfaces 424 and is never pumped to thermal pads 24. The cooling of surfaces 424 cools the fluid inside of cartridge 400, which is pumped to thermal pads 24 to cool the patient. In a modified embodiment, cartridge 400 and thermal control unit 222 can be modified so that fluid inside of cartridge 400 flows, either partially or wholly, into one or more fluid passageways built into thermal control unit 222.

When cartridge 400 is inserted into receptacle 416 of thermal control unit 22, one of the controllers 264 and 422 acts as a master controller and the other acts as a slave controller, in at least some embodiments. Whichever controller is acting as the master controller then carries out thermal treatment of the fluid circulating inside of cartridge 400 in any of the manners described above with respect to cooling units 52 and 54. That is, cooling units 252 and 254 of system 220 are controlled in the same manners as first and second cooling units 52 and 54 of system 20. Thus, the master controller may apportion the cooling work between the two cooling units 252 and 254 according to the efficiency, noise, the respective cooling capacities of each of the cooling units 252 and 254, the anticipated future cooling needs of the system 220, and/or other factors.

In some embodiments, cooling unit 254 is constructed in any of the same manners described above with respect to cooling unit 54. As a result, in some embodiments cooling units 252 and 254 have different cooling capacities, while in other embodiments they have the same cooling capacities. At least one of cooling units 252 and 254 may also or additionally include a variable speed compressor, a variable speed fan 88, and/or a pre-cooling unit 106. One or both of the cooling units 252 and 254 may also include an ambient air temperature sensor used to measure the temperature of the air delivered by fan 88. This temperature may be used by the respective controller to control the fan speed and/or the compressor speed, and/or for other purposes. Still other features and functions of cooling units 52 and 54 described above may be incorporated into cooling units 252 and 254, as well additional functions and features not described previously.

Cartridge 400 and/or thermal control unit 222 are adapted to detect when cartridge 400 is inserted into receptacle 416. This detection may be accomplished in a variety of different manners. In one embodiment, thermal control unit 222 includes a sensor positioned adjacent receptacle 416 that detects the presence of cartridge 400 and reports this to controller 264. Alternatively, or additionally, cartridge 400 includes a sensor that detects when it is positioned inside of thermal control unit 222. Still further, in those embodiments where controller 422 is adapted to wirelessly communicate with controller 264, detection may be carried out through the ability of controllers 422 and 264 to successfully communicate using near field and/or another short range communication technology. That is, if cartridge 400 is in close proximity to thermal control unit 222 such that such short range communication is able to take place, the successful ability to wirelessly communicate may be used as a proxy for indicating that cartridge 400 is currently inserted into thermal control unit 222. The ability to communicate via a wired connection between controllers 264 and 422 may alternatively be used as an indication of the presence of cartridge 400 in receptacle 416. Still other detection schemes may be used.

After cartridge 400 is inserted into receptacle 416 of thermal control unit 222, controller 264 is adapted, in at least some embodiments, to transfer a thermal history log maintained in a memory of cartridge 400 to controller 422 of thermal control unit 222. Controller 422 analyzes this thermal history log and stores it in a memory inside of thermal control unit 222. The content of the thermal history log includes data gathered during the thermal treatment of a patient that occurred when cartridge 400 was used alone to thermally treat a patient. This data includes, but is not limited to, a current target temperature for the patient, past and current readings of the patient's temperature, past and current readings of the temperature of the fluid circulating in circulation channel 248, timestamps for all of the temperature readings, alarms or other notable events, and/or other data. In some embodiments, the transfer of this thermal history data is carried out in any of the manners disclosed in commonly assigned U.S. patent application Ser. No. 62/346, 583 filed Jun. 7, 2016, by inventors Gregory Taylor et al. and entitled THERMAL CONTROL SYSTEM, the complete disclosure of which is hereby incorporated herein by reference.

After cartridge 400 is inserted inside thermal control unit 222 and the thermal history data from cartridge 400 has been transferred to controller 422, controller 422 automatically continues with whatever thermal treatment cartridge 400 is or was recently carrying out. If controller 264 was not carrying out any thermal treatment at or near the time cartridge 400 is inserted into thermal control unit 222, controller 422 does not automatically commence with any thermal treatment, but instead waits until a user inputs treatment instructions via user interface 40. Once such instructions are input, controller 422 carries out the necessary cooling of the fluid inside of cartridge 400 by simultaneously controlling the cooling of either or both of cooling units 252 and/or 254, as discussed above.

Thermal control unit 222 includes at least one temperature sensor 426 (FIG. 5) that controller 422 uses for automatically adjusting the temperature of the circulating fluid inside of cartridge 400 to match a desired temperature. Temperature sensor 426 provides feedback to controller 422 so that closed-loop control of the temperature of the fluid delivered to outlet 404 can be obtained. Cartridge 400 also includes at least one temperature sensor 410*a*, *b*, and/or *c* that controller 264 uses when cartridge 400 is decoupled from thermal control unit 222 and is delivering temperature-controlled fluid to a patient. Specifically, when cartridge 400 is decoupled from control unit 222, controller 264 uses the outputs of these one or more temperature sensors 410*a-c* in order to adjust the commands delivered to cooling unit 252. When cartridge 400 is coupled to thermal control unit 222, controller 264 forwards the outputs from the temperature sensors 410*a-c* to controller 422 (when controller 422 is acting as the master controller). Controller 422 then utilizes the temperature readings from sensors 410*a-c* and 426 to provide commands to cooling units 252 and 254 and send control signals to valve 408.

By providing a separate cartridge 400 that is removable from thermal control unit 222, control system 220 provides a more convenient and flexible temperature control system. For example, in many embodiments, cartridge 400 is smaller and more portable than thermal control unit 222. As a result, cartridge 400 can be used in an ambulance or in other locations outside of a medical facility. When a patient is brought into a medical facility, cartridge 400 can be inserted into thermal control unit 222 and the thermal treatment of the patient can seamlessly continue. In still other embodiments, cartridge 400 is adapted to be inserted into a smaller and more portable thermal control unit than thermal control unit 222. In these embodiments, cartridge 400 may be used in the field (e.g. outside a healthcare facility) with a relatively small and portable thermal control unit and subsequently switched to the larger and less portable thermal control unit 222 when used inside the healthcare facility. Still other ways of using cartridge 400 and thermal control unit 222 together are possible.

In addition to the capabilities previously described herein, thermal control unit 22 and/or 222 may be modified to detect when shivering occurs within a patient undergoing thermal treatment using thermal control systems 20 or 220. The detection of such shivering may be carried out in any of the manners disclosed in commonly assigned U.S. patent application Ser. No. 62/425,813 filed Nov. 23, 2016, by inventors Gregory Taylor et al. and entitled THERMAL SYSTEM, the complete disclosure of which is incorporated herein by reference. Other manners of detecting shivering may also be incorporated into either or both of the thermal control units 22 and 222.

In addition to all of the modifications to thermal control system 220 that have been previously described, cartridge 400 of thermal control system 220 may be further modified to include a bypass line similar to bypass line 66 of thermal control unit 22. Such a bypass line allows fluid within cartridge 400 to circulate inside of circulation channel 248 prior to cartridge 400 being coupled to one or more thermal pads 24, thereby enabling the temperature of the circulating fluid to be adjusted more easily while no thermal pads 24 are connected. Cartridge 400 and/or thermal control unit 222 may alternatively or additionally be modified to include one or more heaters. The inclusion of one or more heaters expands the heat transfer capacities of cartridge 400 and/or control unit 222 beyond mere cooling, and allows thermal control system 220 to warm patients as well as cool patients. Such heaters may also allow controller 264 and/or 422 to control the temperature of the circulating fluid with greater precision.

Thermal control unit 222 may also, or alternatively, be modified to include its own fluid outlet and fluid inlet so that it is able to provide temperature treated fluid to a patient in situations where a fluid cartridge 400 is not available. When a cartridge 400 is available, the modified thermal control unit 222 can provide temperature controlled fluid to a patient that originates both from its own source and from a fluidly isolated source within cartridge 400, or the user can select which source of temperature controlled fluid to use (or the selection can be carried out automatically be controller 64).

The thermal therapy pads 24 used with either of thermal control systems 20 and 220 may vary greatly. In some embodiments, thermal therapy pads of the type disclosed in commonly assigned U.S. patent application Ser. No. 62/373, 658 filed Aug. 11, 2016, by inventors James K. Galer et al. and entitled THERMAL THERAPY DEVICES may be used. In other embodiments, thermal therapy pads of the type disclosed in commonly assigned U.S. patent application Ser. No. 62/373,564 filed Aug. 11, 2016, by inventor James K. Galer and entitled THERMAL SYSTEM may also or alternatively be used. The entire disclosures of both of these applications are hereby incorporated herein by reference. Appropriate modifications to thermal control unit 22 and/or 222 may be made, as necessary, in order for these control units to operate with the types of thermal pads disclosed in these two patent applications.

Various other alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a patient's temperature, the thermal control unit comprising:
    a fluid outlet adapted to fluidly couple to a fluid supply line;
    a fluid inlet adapted to fluidly couple to a fluid return line;
    a circulation channel coupled to the fluid outlet and the fluid inlet;
    a pump for circulating fluid through the circulation channel from the fluid inlet to the fluid outlet;
    a first cooling unit in thermal communication with the circulation channel, the first cooling unit adapted to cool the circulating fluid and including a first compressor;
    a second cooling unit in thermal communication with the circulation channel and positioned downstream of the first cooling unit, the second cooling unit adapted to cool the circulating fluid and including a second compressor; and a controller in communication with the first and second cooling units, the controller adapted to selectively enable and disable the first cooling unit based at least partially upon a temperature of the fluid.

2. The thermal control unit of claim 1 wherein the first cooling unit has a first heat transfer capacity and the second cooling unit has a second heat transfer capacity, the second heat transfer capacity being different from the first heat transfer capacity.

3. The thermal control unit of claim 1 wherein the controller is further adapted to selectively enable and disable the second cooling unit based at least partially upon the temperature of the fluid.

4. The thermal control unit of claim 3 wherein the controller is further adapted to automatically enable both the first and second cooling units when the thermal control unit initially begins cooling the fluid, and to thereafter automatically disable one of the first and second cooling units based at least partially upon the temperature of the fluid.

5. The thermal control unit of claim 1 further including a patient temperature port adapted to receive a patient temperature probe adapted to detect the patient's temperature, the patient temperature port communicating the patient's temperature to the controller, and wherein the controller is further adapted to selectively enable and disable the first cooling unit based partially upon the patient's temperature.

6. The thermal control unit of claim 1 wherein the controller is further adapted to control a first rate of cooling of the first cooling unit and a second rate of cooling of the second cooling unit.

7. The thermal control unit of claim 6 wherein the first cooling unit further comprises a first condenser and a first evaporator; and wherein the second cooling unit further comprises a second condenser and a second evaporator.

8. The thermal control unit of claim 7 wherein the controller is adapted to control the first rate of cooling by controlling a first valve positioned between the first evaporator and the first compressor; and the controller is further adapted to control the second rate of cooling by controlling a second valve positioned between the second evaporator and the second compressor.

9. The thermal control unit of claim 7 further comprising a fan adapted to blow ambient air on the first condenser, wherein the controller is further adapted to control a speed of the fan.

10. The thermal control unit of claim 1 further comprising an ambient air temperature sensor in communication with the controller, the controller further adapted to selectively enable and disable the first cooling unit based at least partially upon a temperature sensed by the ambient air temperature sensor.

11. A thermal control unit for controlling a patient's temperature, the thermal control unit comprising:
  a housing;
  a cartridge adapted to be removably positioned within the housing, the cartridge including a fluid outlet adapted to fluidly couple to a fluid supply line, a fluid inlet adapted to fluidly couple to a fluid return line, a circulation channel coupled to the fluid outlet and the fluid inlet, a first cooling unit in thermal communication with the circulation channel, and a first controller adapted to control the first cooling unit, the first cooling unit adapted to cool a fluid within the circulation channel;
  a second cooling unit positioned within the housing and external to the cartridge the second cooling unit adapted to cool the fluid within the circulation channel; and
  a second controller adapted to control the second cooling unit, wherein the first and second controllers are adapted to communicate with each other when the cartridge is positioned within the housing and to coordinate control of the first and second cooling units in order to control a temperature of the fluid in the circulation channel.

12. The thermal control unit of claim 11 wherein the first cooling unit has a first heat transfer capacity and the second cooling unit has a second heat transfer capacity, the second heat transfer capacity being larger than the first heat transfer capacity.

13. The thermal control unit of claim 11 wherein the fluid circulates inside the housing only within the cartridge.

14. The thermal control unit of claim 11 wherein the first cooling unit comprises a first compressor, a first condenser, a first evaporator, and a first refrigerant; the second cooling unit comprises a second compressor, a second condenser, a second evaporator, and a second refrigerant; and wherein the first refrigerant is fluidly isolated from the second refrigerant when the cartridge is positioned within the housing.

15. The thermal control unit of claim 11 further comprising:
  a battery positioned within the cartridge and adapted to provide electrical power to the first cooling unit when the cartridge is removed from the housing; and
  a plug coupled to the housing and adapted to carry electrical power from a wall outlet to the housing to provide electrical power to the second cooling unit.

16. The thermal control unit of claim 11 wherein the first cooling unit comprises a first compressor, a first condenser, and a first evaporator; the second cooling unit comprises a second compressor, a second condenser, and a second evaporator; and wherein the first controller is adapted to selectively enable and disable the first cooling unit.

17. The thermal control unit of claim 16 wherein the second controller is adapted to send instructions to the first controller instructing it to selectively enable and disable the first cooling unit based at least partially upon the temperature of the fluid.

18. A thermal control unit for controlling a patient's temperature, the thermal control unit comprising:
  a fluid outlet adapted to fluidly couple to a fluid supply line for delivering fluid to the patient;
  a fluid inlet adapted to fluidly couple to a fluid return line for receiving fluid returned from the patient;
  a fluid circulation channel coupled to the fluid outlet and the fluid inlet;
  a pump for circulating fluid through the fluid circulation channel from the fluid inlet to the fluid outlet;
  a first cooling unit adapted to cool fluid circulating through the fluid circulation channel, the first cooling unit including a compressor, an evaporator, and a condenser;
  a fan adapted to blow ambient air onto the condenser;
  a pre-cooling unit positioned adjacent the fan and adapted to pre-cool the ambient air blown onto the condenser by the fan; and
  a controller adapted to selectively control a speed of the fan based at least upon a temperature of the fluid circulating through the fluid circulation channel, the controller further adapted to divert at least a portion of the fluid from the fluid circulation channel into the pre-cooling unit whereby the diverted fluid is used to pre-cool the ambient air blown onto the condenser.

19. The thermal control unit of claim 18 wherein the controller controls an amount of fluid diverted to the pre-cooling unit based at least partially upon a temperature of the patient.

20. The thermal control unit of claim 18 further comprising a second cooling unit adapted to cool fluid circulating through the fluid circulation channel, the second cooling unit including a second compressor, a second evaporator, and a second condenser.

21. The thermal control unit of claim 20 wherein the controller is adapted to change a first rate of cooling of the first cooling unit without changing a second rate of cooling of the second cooling unit, and vice versa.

22. The thermal control unit of claim 20 wherein the controller is adapted to disable the second cooling unit by ceasing circulation of a refrigerant through the second cooling unit, but by continuing to allow the pump to circulate fluid through the fluid circulation channel.

23. The thermal control unit of claim 20 wherein the second cooling unit is contained within a cartridge adapted to be removably positioned within a housing of the thermal control unit, and the first cooling unit is contained within the housing outside of the cartridge.

* * * * *